(12) United States Patent
Cooper et al.

(10) Patent No.: US 9,581,493 B2
(45) Date of Patent: Feb. 28, 2017

(54) ACQUIRING A RAMAN SPECTRUM WITH MULTIPLE LASERS

(71) Applicant: Bruker Optics, Inc., Billerica, MA (US)

(72) Inventors: John B. Cooper, Virginia Beach, VA (US); Mohamed F. Abdelkader, Norfolk, VA (US); Kent L. Wise, The Woodlands, TX (US)

(73) Assignee: Bruker Optics, Inc., Billerica, MA (US)

( * ) Notice: Subject to any disclaimer, the term of this patent is extended or adjusted under 35 U.S.C. 154(b) by 0 days.

(21) Appl. No.: 14/179,200

(22) Filed: Feb. 12, 2014

(65) Prior Publication Data
US 2015/0226607 A1    Aug. 13, 2015

(51) Int. Cl.
| | |
|---|---|
| *G01J 3/44* | (2006.01) |
| *G01J 3/10* | (2006.01) |
| *G01N 21/65* | (2006.01) |
| *G01J 3/02* | (2006.01) |

(52) U.S. Cl.
CPC .............. *G01J 3/10* (2013.01); *G01J 3/027* (2013.01); *G01J 3/44* (2013.01); *G01N 21/65* (2013.01)

(58) Field of Classification Search
CPC  G01N 21/65; G01N 21/658; G01N 2021/656; G01J 3/44; G01J 3/02
USPC ........................................................ 356/301
See application file for complete search history.

(56) References Cited

U.S. PATENT DOCUMENTS

| | | | | |
|---|---|---|---|---|
| 6,061,134 | A * | 5/2000 | Jensen ...................... | G01J 3/44 356/451 |
| 6,507,401 | B1* | 1/2003 | Turner et al. ................ | 356/436 |
| 7,420,664 | B2* | 9/2008 | Treado ...................... | G01J 3/02 356/72 |
| 7,787,117 | B1 | 8/2010 | Leona et al. | |
| 2005/0030540 | A1* | 2/2005 | Thornton ...................... | 356/432 |
| 2005/0100068 | A1* | 5/2005 | Jikutani et al. ................. | 372/46 |
| 2005/0248758 | A1* | 11/2005 | Carron ...................... | G01J 3/02 356/301 |
| 2007/0223541 | A1* | 9/2007 | Van Saarloos .................. | 372/22 |
| 2008/0239307 | A1* | 10/2008 | Talley et al. ................... | 356/301 |
| 2009/0204110 | A1* | 8/2009 | Islam ................................ | 606/9 |
| 2010/0291599 | A1 | 11/2010 | Tague, Jr. et al. | |
| 2011/0247401 | A1* | 10/2011 | Schwartz et al. .............. | 73/40.7 |
| 2014/0161459 | A1* | 6/2014 | Ho et al. ......................... | 398/79 |

OTHER PUBLICATIONS

Delivering the World's Higest Power Monolithic DBR Laser Diodes, Mercury TOSA Package for High Power DBR Lasers, http://photodigm.com/Mercury-TOSA-Package-Description/.

* cited by examiner

*Primary Examiner* — Tarifur Chowdhury
*Assistant Examiner* — Md M Rahman
(74) *Attorney, Agent, or Firm* — O'Shea Getz P.C.

(57) ABSTRACT

A spectrometer is provided for acquiring a Raman spectrum from a sample. The spectrometer includes a first laser, a second laser, a detector and a processing device. The first laser is adapted to produce a first laser beam for generating first Raman spectra from the sample. The second laser is adapted to produce a second laser beam for generating second Raman spectra from the sample. The detector is adapted to collect the first Raman spectra and the second Raman spectra. The processing device is adapted to process the collected first and second Raman spectra to provide the Raman spectrum.

24 Claims, 16 Drawing Sheets

ACQUIRING A RAMAN SPECTRUM WITH MULTIPLE LASERS

FIELD OF TECHNOLOGY

The disclosure relates to methods and devices for acquiring a Raman spectrum.

BACKGROUND

A vibrational spectrum of molecules, ionic compounds, and polyatomic ions may be generated using Raman spectroscopy. This vibrational spectrum may be used to identify a sample of a unique chemical or a unique mixture of chemicals much as a fingerprint is used to identify a person.

To generate a Raman spectrum, a sample is irradiated with a monochromatic excitation source. This monochromatic excitation source provides spectral resolution in the Raman spectrum. By contrast, a broadband source may generate broad vibrational peaks in the vibrational spectrum.

Typically, when photons from a monochromatic excitation source impinge a sample, a majority of the photons are scattered elastically resulting in a Rayleigh scattering of light. This scattering of light has the same wavelength as the excitation source. The excitation source therefore should be relatively intense in order to generate a Raman signal that may be relatively easily detected. As a result, lasers are almost exclusively used as the monochromatic excitation source in conventional Raman spectrometers.

The efficiency of Raman scattering is inversely proportional to the laser wavelength raised to the fourth power. It is easier therefore to generate a detectable signal using a laser with a relatively short wavelength. A short wavelength laser, however, may have a relatively large amount of energy per photon, which can result in the generation of fluorescence due to the population of excited electronic states within the sample or within impurities included in the sample. Fluorescence generation is typically many orders of magnitude more efficient than Raman scattering. Using a short wavelength laser therefore often results in a spectrum with a fluorescence signal that is much larger than the Raman signal and may prevent the Raman signal from being accurately measured. Thus, there are both advantages and disadvantages for any laser wavelength that might be selected. Many commercial instruments therefore include a plurality of excitation lasers so that a user may select which laser wavelength is appropriate for a particular measurement.

The Raman signal is detected with a detector sensitive to the Raman photons generated by the laser. A typical detector includes a plurality of charge-couple-devices (CCDs). These CCDs enable a spectrum with a relatively high signal to noise ratio to be obtained due to the nature of the CCDs. For example, a silicon-based CCD detector may be made in an array format so that Raman photons of different wavelengths may be detected substantially simultaneously by dispersing the photons spatially across the CCD. This multiplex effect allows the entire Raman vibrational spectrum of a sample to be detected with a single measurement.

For a sample that gives rise to strong fluorescence as discussed above, it is desirable to use a long wavelength laser so that the excited states of the sample are not populated efficiently. A typically CCD detector, however, is not sufficiently sensitive to photons with a wavelength greater than 1100 nanometers (nm). This presents a dilemma since it is common to distinguish chemicals based on vibrations due to carbon-hydrogen (CH), oxygen-hydrogen (OH), and nitrogen-hydrogen (NH) bond stretching. These vibrations generally occur at absolute energies between 2700-3300 wave numbers. When used in combination with vibrations of lower energy (e.g., the "fingerprint" region), a significant advantage is realized.

To observe the hydrogen stretching vibrations with a CCD detector that detects photons at wavelengths shorter than 1100 nm, the excitation laser should be less than 807 nm. For this reason, one of the most common lasers used in an excitation source is a 785 nm wavelength laser. Use of a 785 nm wavelength laser, however, often results in generation of significant fluorescence. Thus, it is desirable to use a longer wavelength laser in order to reduce fluorescence. Use of a longer wavelength laser, however, may result in the loss of important vibrational information about the chemical sample since the vibrations due to carbon-hydrogen (CH), oxygen-hydrogen (OH), and nitrogen-hydrogen (NH) bond stretching occur at wavelengths which are not detectable by a silicon CCD. Furthermore, less expensive CCDs typically cannot efficiently detect photons with wavelengths above 1060 nm. For example, the CCDs typically used in handheld Raman instruments cannot detect the laser wavelengths greater than 785 nm that include the important CH, OH, NH bond stretching vibrations.

Longer wavelength lasers in combination with detectors that are sensitive to longer wavelength photons may be used during Raman spectrometry. For example, an FT-Raman spectrometer typically includes a 1064 nm wavelength laser and a single element detector based on germanium or indium gallium arsenide in combination with an interferometer. Although FT-Raman spectrometer detects substantially the entire Raman spectrum including the CH, OH, and NH stretching region, this spectrometer has other deficiencies. In particular, the laser wavelength of the FT-Raman spectrometer is so long that in order to generate a sufficient Raman signal, a high optical power is used that may result in sample burning. This problem is compounded since germanium (Ge) detectors and indium gallium arsenide (InGaAs) detectors generate a higher noise level than silicon detectors such as CCDs. This poor performance relative to a CCD detector results in a lower quality spectrum or the requirement of a much longer acquisition time.

In a second example, a spectrometer is configured with InGaAs array detectors and a long (e.g., 1064 nm) wavelength laser. Although the InGaAs array detectors provide a multiplex advantage similar to a CCD, this spectrometer may also cause sample burning as described above. Furthermore, even with the addition of the multiplex effect, the InGaAs array detectors are still noisier than CCD detectors and thus have a worse quality signal-to-noise ratio. This is compounded by fixed pattern noise due to non-uniformity of the individual InGaAs detector elements (pixels) which make the InGaAs array detector.

In a third example, a spectrometer is configured with a short wavelength laser (e.g., 785 nm wavelength laser) with a CCD detector, and a long wavelength laser (e.g., 1064 nm wavelength laser) with an InGaAs array detector. This configuration allows a user to select traditional CCD detection (e.g., with 785 nm laser excitation) for samples which exhibit negligible or low fluorescence, or to select InGaAs array detection (e.g., with 1064 nm laser excitation) for samples which exhibit significant fluorescence. Effectively providing two Raman spectrometers, however, dramatically increases cost, size, and complexity of the spectrometer. In addition, this spectrometer still suffers from the poor signal to noise of the InGaAs array detector for part of the vibrational information.

As described above, prior art spectrometers are unable to use laser wavelengths long enough to significantly reduce fluorescence relative to a 785 nm wavelength laser, while still being detectable by a CCD detector and providing the vibrational spectral region including CH, OH, and NH vibrations. In addition, these spectrometers also suffer from a spectral resolution problem. For example, since the Raman signal is dispersed spatially across the CCD as a function of wavelength, the resolution between vibrational peaks may be limited by the size of the CCD detector. Therefore, in order to observe both the fingerprint region and the hydrogen stretching region with good resolution, a relatively large CCD detector should be used (e.g., one inch or larger in length). However, such a relatively large CCD adds significant expense to the spectrometer.

There is a need in the art for an improved method and apparatus for acquiring Raman spectra.

SUMMARY OF THE INVENTION

According to a first aspect, a spectrometer is provided for acquiring a Raman spectrum from a sample. The spectrometer includes a first laser, a second laser, a detector and a processing device. The first laser is adapted to produce a first laser beam for generating first Raman spectra from the sample. The second laser is adapted to produce a second laser beam for generating second Raman spectra from the sample. The detector is adapted to collect the first Raman spectra and the second Raman spectra. The processing device is adapted to process the collected first and second Raman spectra to provide the Raman spectrum.

According to a second aspect, another spectrometer is provided for acquiring a Raman spectrum from a sample. The spectrometer includes an excitation source, a detector and a processing device. The excitation source is adapted to produce a laser beam for generating Raman spectra. The laser beam is produced with a first wavelength during a first mode of operation. The laser beam is produced with a second wavelength during a second mode of operation. The first wavelength is different than the second wavelength. The processing device is adapted to combine the Raman spectra collected during the first and the second modes of operation to provide the Raman spectrum.

According to a third aspect, another spectrometer is provided for acquiring a Raman spectrum from a sample. The spectrometer includes a distributed Bragg reflector diode first laser, a distributed Bragg reflector diode second laser, and a detector. The first laser is adapted to produce a first laser beam for generating first Raman spectra from the sample. The second laser is adapted to produce a second laser beam for generating second Raman spectra from the sample. The detector is adapted to collect the first Raman spectra and the second Raman spectra.

According to a third aspect, another spectrometer is provided for acquiring a Raman spectrum from a sample. The spectrometer includes an excitation source, a laser filter and a detector. The excitation source is adapted to produce a laser beam for generating Raman spectra. The laser beam travels through the laser filter towards the sample. The laser filter is adapted to pass two discrete wavelength bands of laser beam light. The detector is adapted to collect the Raman spectra.

According to a fourth aspect, a method is provided for acquiring a Raman spectrum from a sample. The method includes directing a first laser beam onto the sample to generate first Raman spectra, wherein the first laser beam has a first wavelength. A second laser beam is directed onto the sample to generate second Raman spectra, wherein the second laser beam has a second wavelength that is different than the first wavelength. The first Raman spectra and the second Raman spectra are collected with a detector. The collected first Raman spectra is combined with the collected second Raman spectra to provide the Raman spectrum.

These and other objects, features and advantages will become more apparent in light of the following detailed description of preferred embodiments thereof, as illustrated in the accompanying drawings.

DETAILED DESCRIPTION OF THE INVENTION

Figure 1:
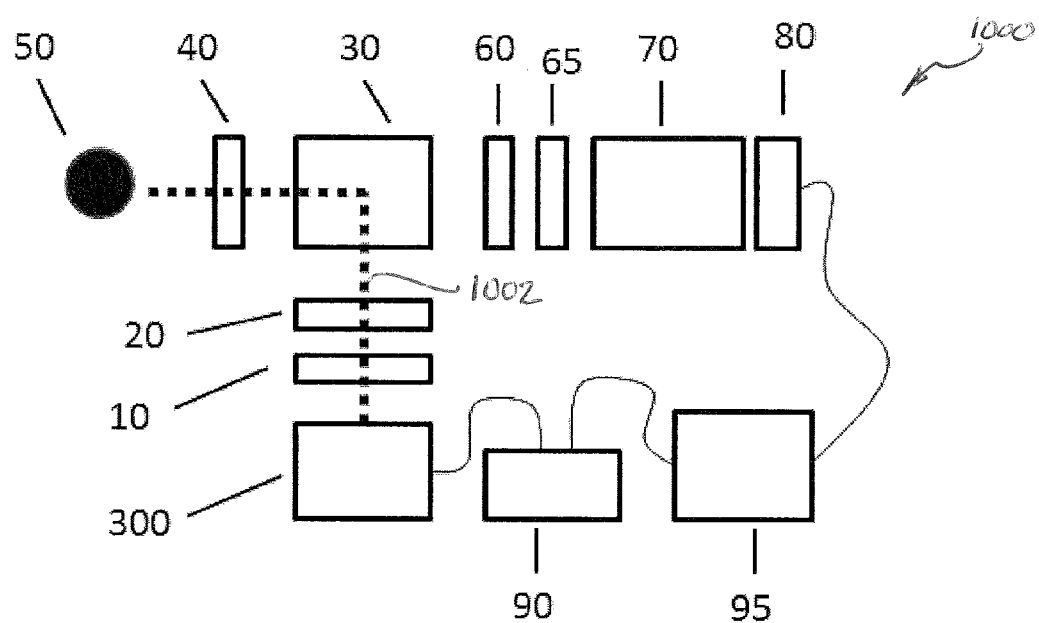
FIG. 1 is a block diagram of a Raman spectrometer with a dual diode laser assembly.
Figure 2:
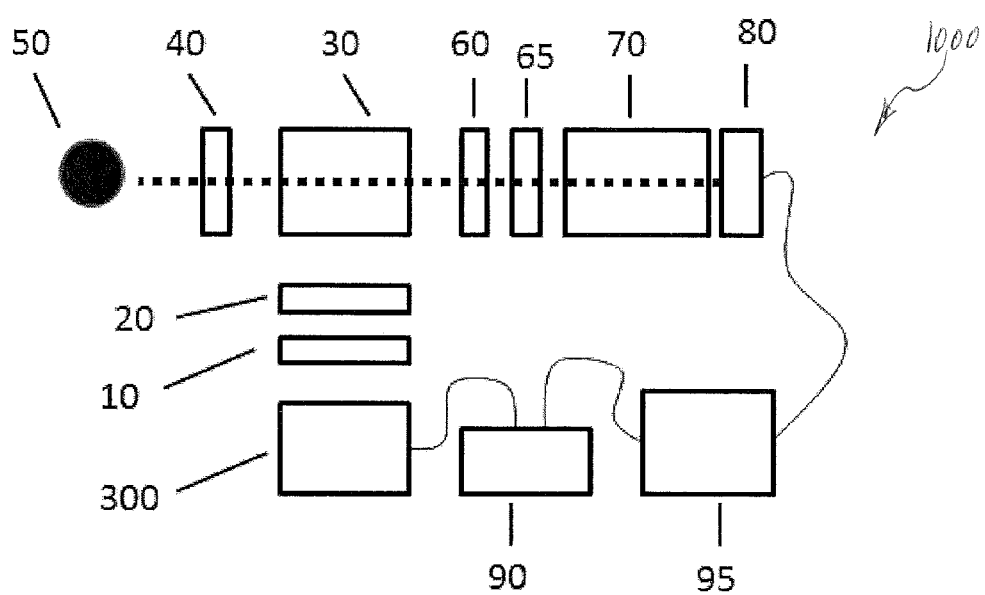
FIG. 2 is another block diagram of the Raman spectrometer of FIG. 1.

FIGS. 1 and 2 illustrate a Raman spectrometer 1000. This spectrometer 1000 includes an excitation source 300 configured with a dual laser source in a TOSA package.

Figure 3:
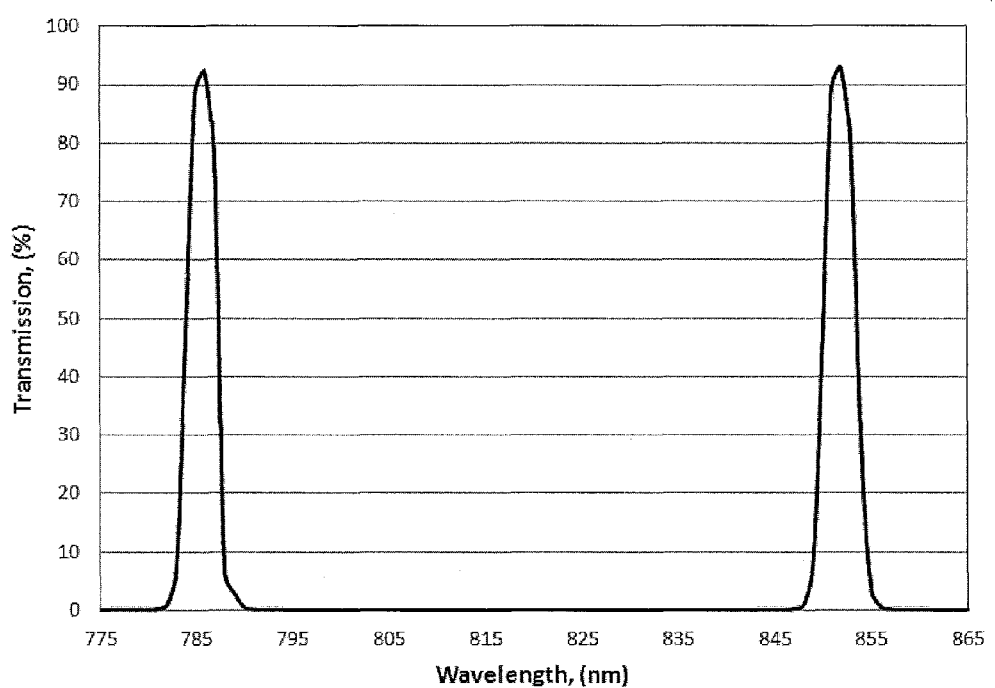
FIG. 3 is a plot of percent (%) transmission of laser light through a laser filter as a function of wavelength of the laser light.

As shown by the dashed line 1002 in FIG. 1, laser light from the excitation source 300 is collimated by a lens 10 and filtered by a laser filter 20. The laser filter 20 is configured with pass bands that pass two relatively narrow wavelength bands of the laser light 1002 while rejecting light outside of the pass-bands. FIG. 3 graphically illustrates percent (%) transmission of the laser light through the laser filter 20 as a function of the wavelength of the laser light for dual excitation lasers with wavelengths of 785 nm and 852 nm.

Referring to FIG. 1, the filtered light passed by the laser filter 20 is reflected by a dichroic beamsplitter 30, which is adapted to transmit light at longer wavelengths than the maximum reflected light. The reflected light is then focused by a lens 40 and directed onto a sample 50 where it generates a Raman signal that includes Raman spectra.

Figure 4:
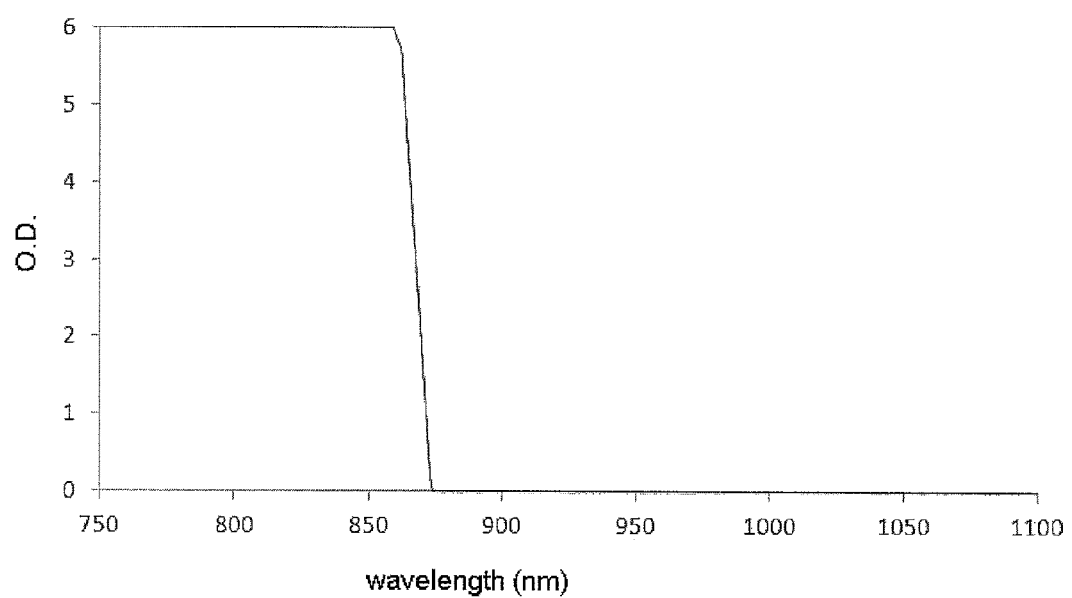
FIG. 4 is a plot of optical density (O.D.) of a laser rejection filter as a function of wavelength for dual excitation lasers at 785 nm and 852 nm.

As shown by the dashed line 1004 in FIG. 2, the Raman signal is collected and collimated by a lens 40. The Raman signal then passes through the dichroic beamsplitter 30 to a long-pass filter 60. The long-pass filter 60 is adapted to remove light from the excitation source 300 and pass the Stokes component of the Raman signal. FIG. 4 illustrates the optical density (O.D.) of the long-pass filter 60 as a function of the wavelength for dual excitation lasers with wavelength of 785 nm and 852 nm. As shown by FIG. 4, the high optical density (O.D.) of the long-pass filter 60 may be selected to substantially only allow the passage of the Stokes component of the Raman signal.

Referring to FIG. 2, the filtered Raman signal is focused by a lens 65 onto the slit of a spectrograph 70. The spectrograph 70 disperses the light onto a detector 80 such as, for example, a CCD detector. Other examples of the detector 80 may include Focal Plane Array detectors such as a Complementary Metal Oxide Semiconductor (CMOS) detector, and Photodiode Array detectors such as an Si detector and an InGaAs detector. Referring again to FIG. 2, a laser diode driver with a temperature controller 90 is electrically connected to the excitation source 300. A microcontroller board 95 is electrically interfaced with the temperature controller 90 and the CCD detector 80.

Figure 5:
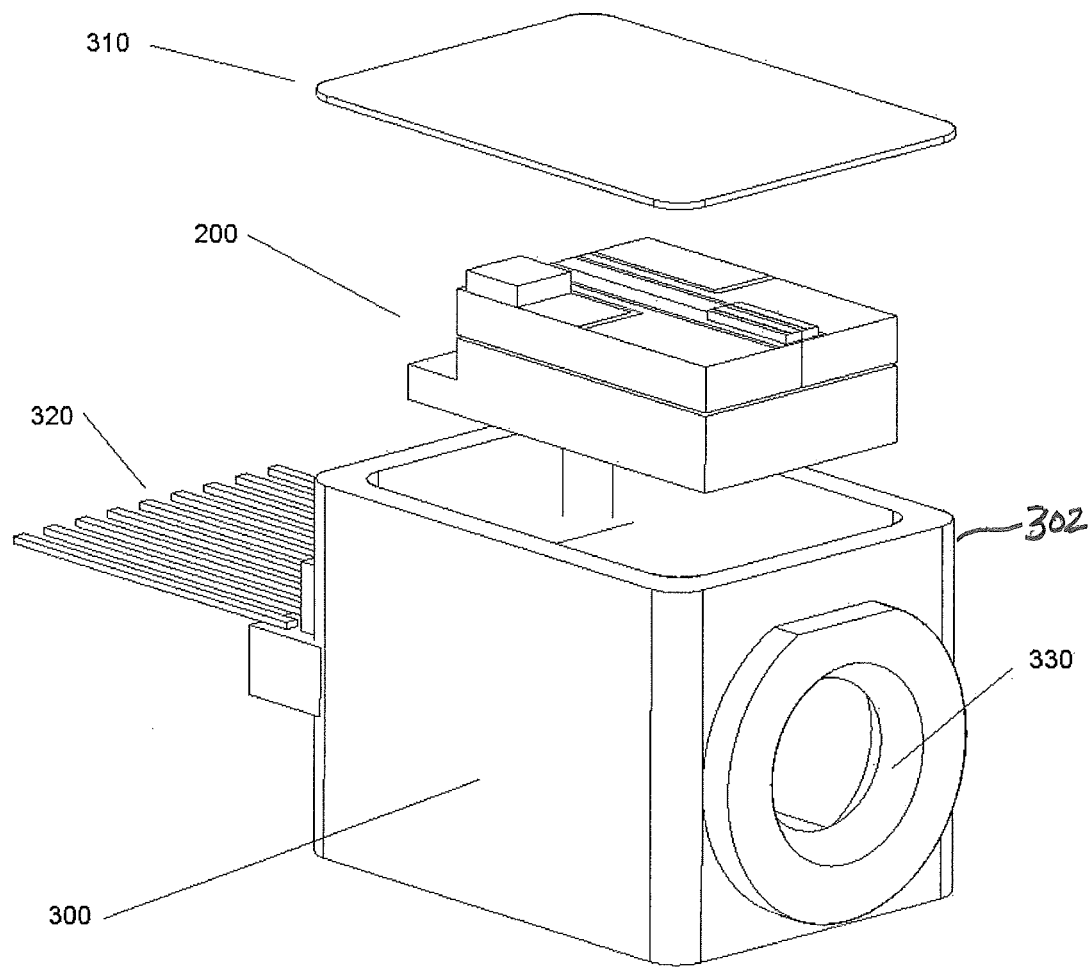
FIG. 5 is a perspective, exploded illustration of an excitation source for the Raman spectrometer of FIG. 1.

Referring to FIG. 5, the excitation source 300 includes a dual laser package 200 and an excitation source housing such as, for example, a TOSA electronic package 302. The dual laser package 200 is located inside of the TOSA electronic package 302. The dual laser package 200, for example, may be soldered to an inside base of the TOSA electronic package 302 to provide thermal contact and mechanical stability. Alternatively, the dual laser package 200 may be fixed to the inside base of the TOSA electronic package 302 using conductive epoxy and/or various other techniques.

The excitation source 300 also includes electrical feed-throughs 320, an exit aperture window 330 and a lid 310. The exit aperture window 330 is positioned in the TOSA electronic package 302 to allow laser light to pass out of the package 302. The electrical feed-throughs 320 are configured to electrically couple the device to the laser diode driver with a temperature controller 90. The lid 310 is configured to hermetically seal the package 302.

Figure 6:
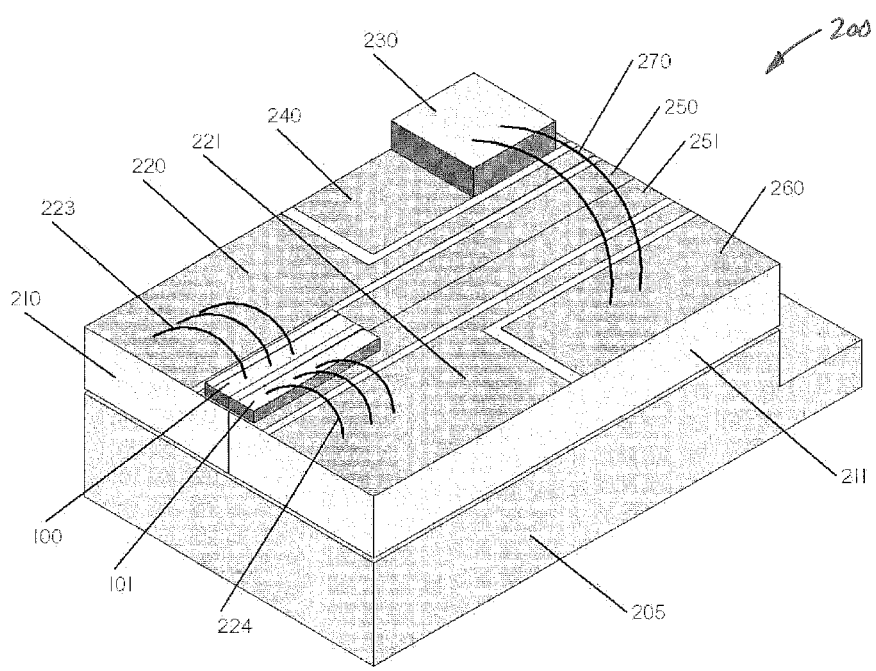
FIG. 6 is a perspective illustration of a dual laser package for the excitation source of FIG. 5.

Referring to FIG. 6, the dual laser package 200 includes a first laser 100 and a second laser 101. The first laser 100 and/or the second laser 101 may each be configured as a distributed Bragg reflector (DBR) diode laser. The present invention, however, is not limited to DBR diode type lasers. One or more of the lasers, for example, may each be configured as a solid state laser such as, for example, a Ti:sapphire laser. One or more of the lasers may also or alternatively each be configured as a semiconductor laser such as, for example, an GaN laser, an InGaN laser, an AlGaInP laser, an AlGaAs laser, an GaAs laser, an InGaAsP laser, an VCSEL laser, a Quantum Cascade laser, and a Hybrid Silicon laser.

The first laser 100 is attached (e.g., soldered) to a conductive (e.g., gold) pad 250 on a surface of a sub-mount 210 made of, for example, aluminum nitride (AlN). The first laser 100 is adapted to emit at a specific wavelength light at a given temperature. For example, the first laser 100 may emit 852 nm wavelength laser light at 25 degrees Celsius (° C.). A conductive (e.g., gold) pad on the surface of the first laser 100 is electrically coupled to another conductive (e.g., gold) pad 223 on the sub-mount 210 surface using (e.g., gold) wires. A surface mount thermistor 230 is electrically coupled to a conductive (e.g., gold) pad 240 on the surface of sub-mount 210. The surface of the thermistor 230 is electrically coupled to a conductive (e.g., gold) pad 260 on the surface of a second sub-mount 211. Each of the pads 223, 240, 250 and 260 on the sub-mounts 210 and 211 are electrically isolated from one another.

The second laser 101 is attached (e.g., soldered) to a conductive (e.g., gold) pad 251 on the surface of the second sub-mount 211 which may be made of AlN. The second laser 101 is adapted to emit at a second specific wavelength light at a given temperature. For example, the second laser 101 may emit 785 nm wavelength laser light at 25° C. A conductive (e.g., gold) pad on the surface of the second laser 101 is electrically coupled using (e.g., gold) wires to another conductive (e.g., gold) pad 221 on the sub-mount 211 surface. Each of the pads on the sub-mount 211 are electrically isolated from one another.

The sub-mounts 210 and 211 are configured together to provide a laser package mount, which may be soldered to an electrically and thermally conducting coating on a surface of a thermoelectric cooler (TEC) 205. Alternatively, the sub-mounts 210 and 211 may be connected to the surface of the thermoelectric cooler 205 using conductive epoxy and/or various other techniques.

Figure 7:
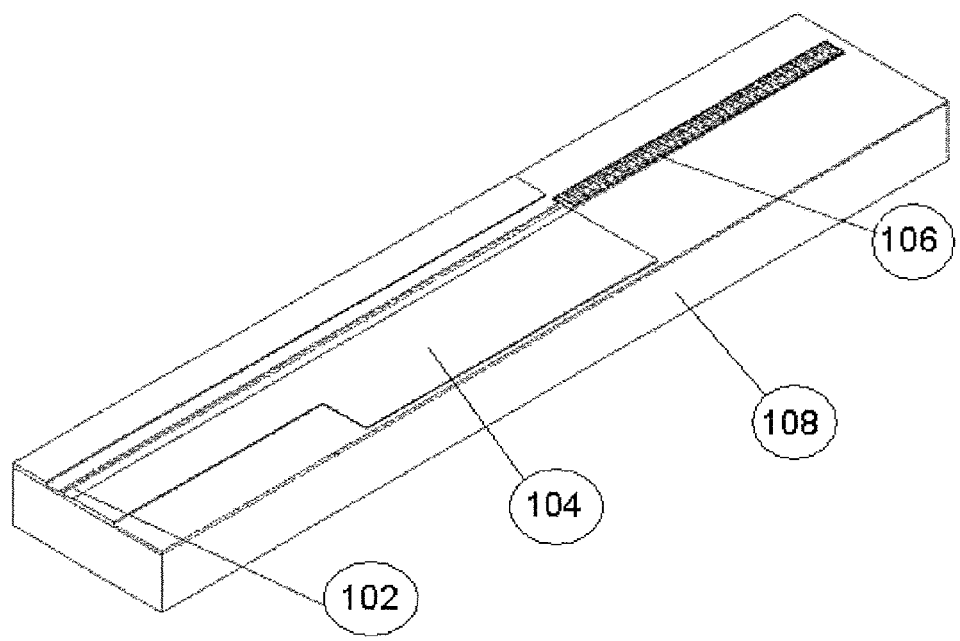
FIG. 7 is a perspective illustration of a distributed Bragg reflector (DBR) diode laser for the dual laser package of FIG. 6.

Referring to FIG. 7, the each laser 100, 101 includes a laser cavity 102 on a top-side of an GaAs substrate 108. A Bragg grating 106 is configured adjacent a rear facet of the laser cavity 102 so that, at a given temperature, light of a specific wavelength is reflected back into the laser cavity 102. The laser light emits from an end of the laser cavity 102 that is opposed to the Bragg grating 106. Each of the lasers 100 and 101 may have a similar configuration as shown in FIG. 6. Alternatively, the second laser 101 may be configured as a mirror image of the first laser 100.

Referring to FIGS. 1, 2 and 7, the excitation source 300 is orientated such that the two images generated by the lasers 100 and 101 at the sample 50 are projected to the slit of the spectrograph so that both images lie on the slit. The separation between the images on the slit is dependent on the spacing between the lasers 100 and 101, and on laser optics. In some embodiments, for example, the spacing and the optics are such that the images at the slit are substantially overlapping and are in the shape of a line which is oriented with the direction of the slit. In other embodiments, the images generated by the two lasers are also oriented in the direction of the slit but have minimal overlap or have spatial separation at the slit. The present invention, of course, is not limited to any particular image shapes and/or orientations.

Figure 8:
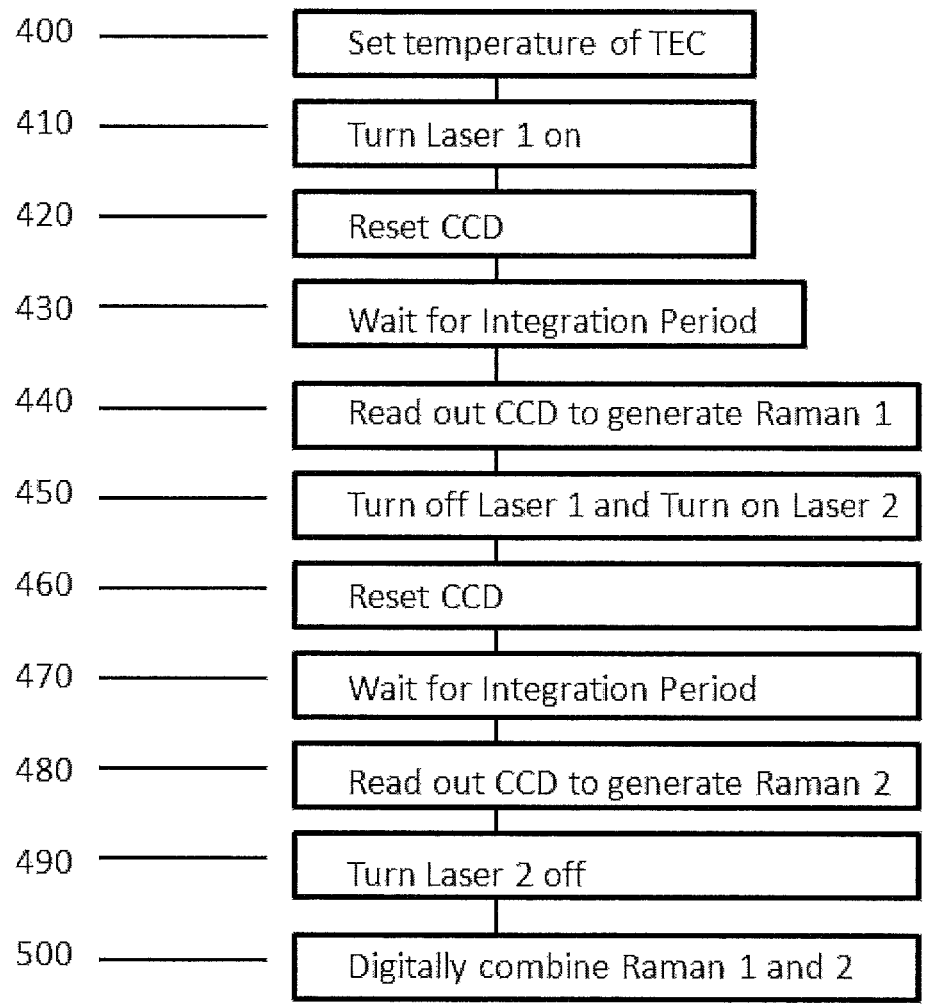
FIG. 8 is a flow diagram of a method for operating the spectrometer of FIGS. 1 and 2.

FIG. 8 is a flow diagram of a method for operating the Raman spectrometer 1000. In step 400, the thermoelectric cooler 205 is set to a predetermined temperature using the temperature controller 90. In step 410, the first laser 100 is turned on. The laser scatters off the sample 50, and the generated Raman is collected and imaged onto the CCD detector 80. In steps 420 and 430, the CCD detector 80 is electronically initialized (e.g., reset) and collects the Raman signal for a predetermined integration period, which starts from the point of time of the initialization. In step 440, the Raman spectrum corresponding to the first laser 100 is read out from the CCD detector. In step 450 the first laser 100 is turned off (e.g., de-energized) and the second laser 101 is turned on. The laser scatters off the sample 50, and the generated Raman is collected and imaged onto the CCD detector 80. In steps 460 and 470, the CCD detector 80 is initialized a second time and is allowed to collect the Raman signal for a predetermined integration period, which starts from the point of time of the second initialization. In step 480, the Raman spectrum corresponding to the second laser 101 is read out from the CCD detector 48. In step 490, the second laser 101 is turned off. In step 500, the two Raman spectra are combined by a processing device (e.g., a computer) to give a single Raman spectrum. This processing device may be configured as part of, or in signal communication with, the spectrometer 1000.

Figure 9:
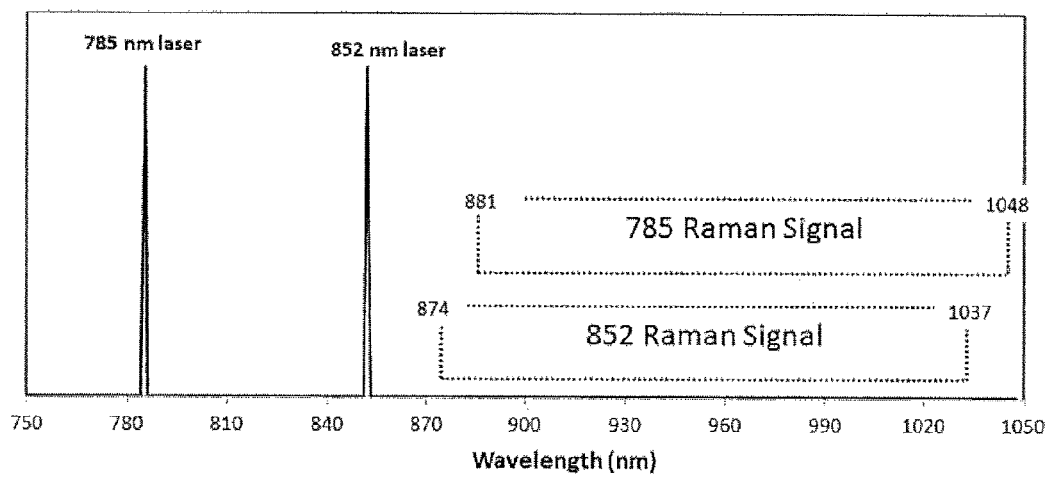
FIG. 9 is a wavelength plot for two laser positions and two Raman spectral regions generated by the two lasers.

FIG. 9 is a wavelength plot for the two laser positions as well as two Raman spectral regions generated by the two lasers 100 and 101. The first laser 100 corresponds to a 785 nm wavelength laser, and the second laser 101 corresponds to an 852 nm wavelength laser. The two Raman spectral regions correspond to the spatial dispersion of the spectra onto the CCD detector 80.

Figure 10:
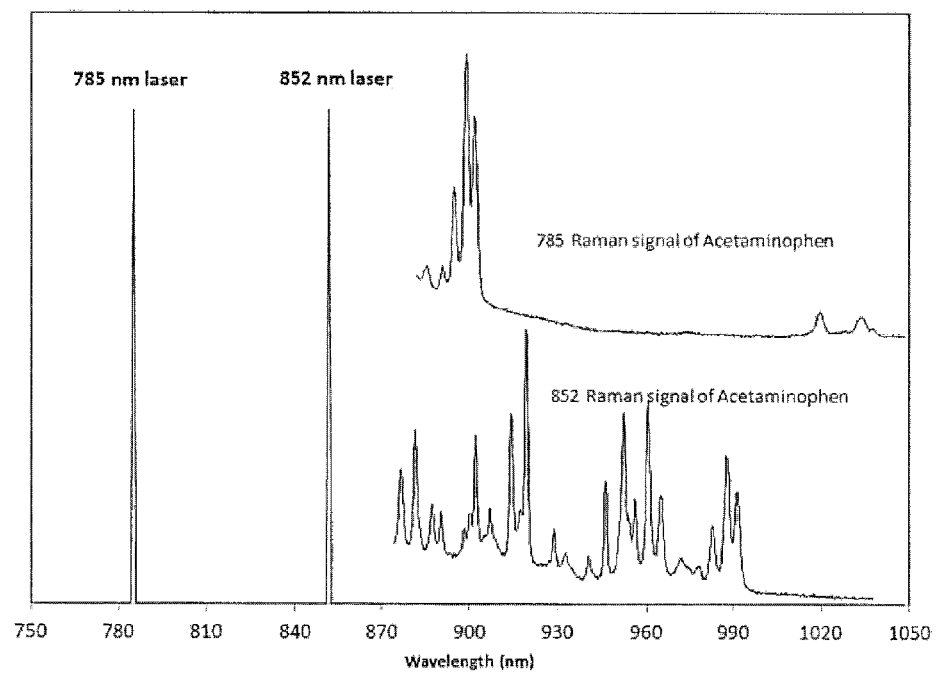
FIG. 10 is another wavelength plot for two laser positions and two Raman spectral regions generated by the two lasers for an acetaminophen sample.

FIG. 10 is a wavelength plot of the actual Raman spectra collected using the lasers 100 and 101 where the sample 50 is acetaminophen. The last portion of the spectrum generated by the 852 nm wavelength laser 101 is duplicated by the first portion of the spectrum generated by the 785 nm spectrum. In addition, the spectrum generated by the 852 nm wavelength laser 101 includes spectral peaks not included in the spectrum generated by the 785 nm wavelength laser 100, and vice versa.

Figure 11:
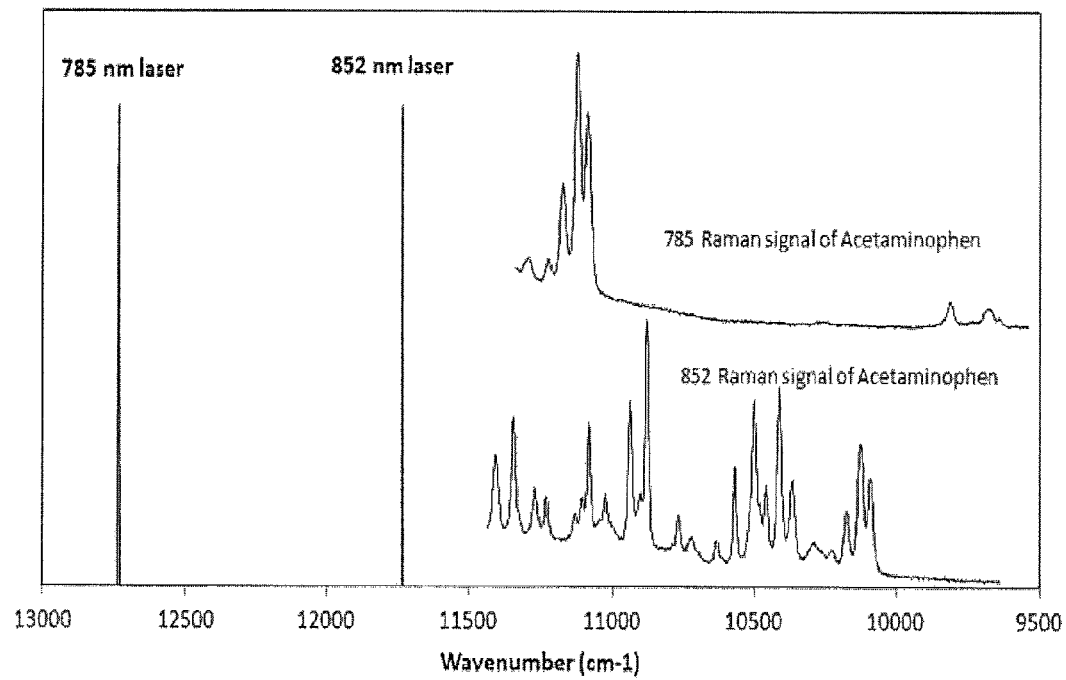
FIG. 11 is a wave number plot for two laser positions and two Raman spectral regions generated by the two lasers for an acetaminophen sample.

FIG. 11 is a wavelength plot similar to that of FIG. 10 except that the axis has been replaced with a wave number axis. Since the 852 nm wavelength laser 101 corresponds to 11737.1 $cm^{-1}$, and the 785 nm wavelength laser 100 corresponds to 12738.9 $cm^{-1}$, the Raman spectral shift can be calculated by subtracting the Raman spectrum wave numbers from the wave number of the laser used to generate the spectrum.

Figure 12:
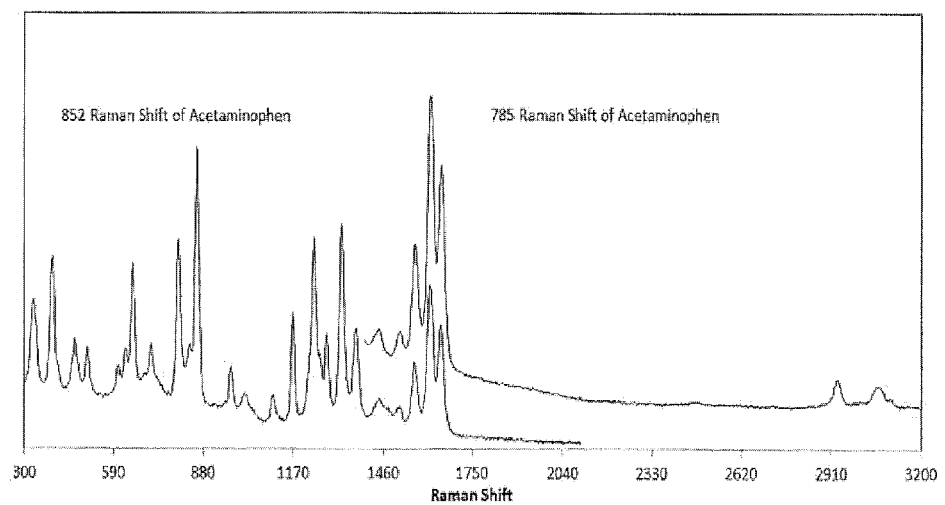
FIG. 12 is a Raman shift plot for two laser positions and two Raman spectral regions generated by the two lasers for an acetaminophen sample.
Figure 13:
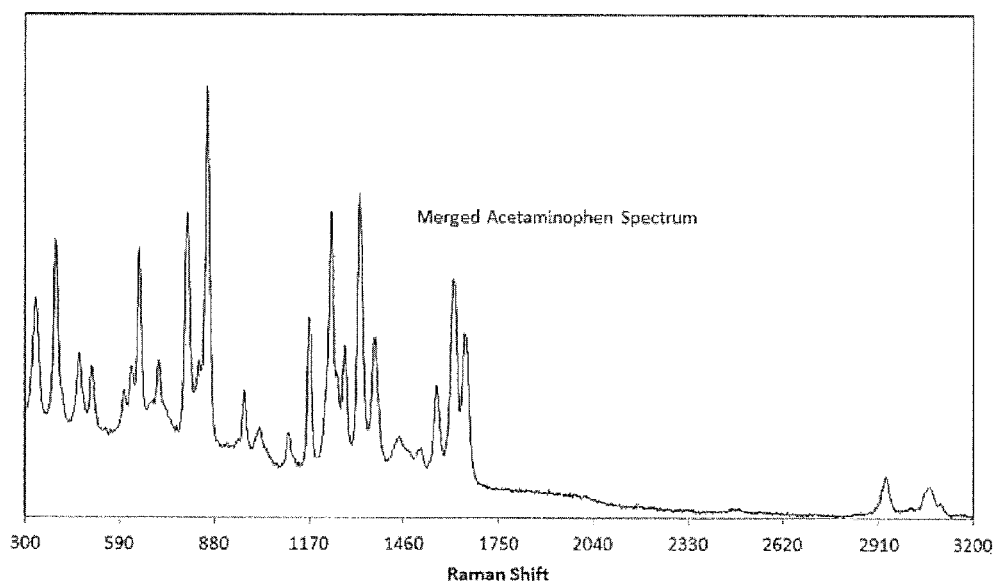
FIG. 13 is another Raman shift plot for two laser positions and two merged Raman spectral regions generated by the two lasers for an acetaminophen sample.

FIG. 12 is a plot of the spectra re-plotted on the Raman shift axis. As shown, the duplicated regions of the two spectra now overlap. A single spectrum is generated by scaling the intensities of the overlapping region and digitally concatenating the spectra at a predetermined tie-point. The result of this is shown in FIG. 13. In FIG. 13, the Raman data generated by the DBR diode lasers 100 and 101 has been used to construct a single spectrum which has greater spectral coverage than either spectrum alone.

Example 1

Simultaneous Dual Laser Excitation

Figure 14:
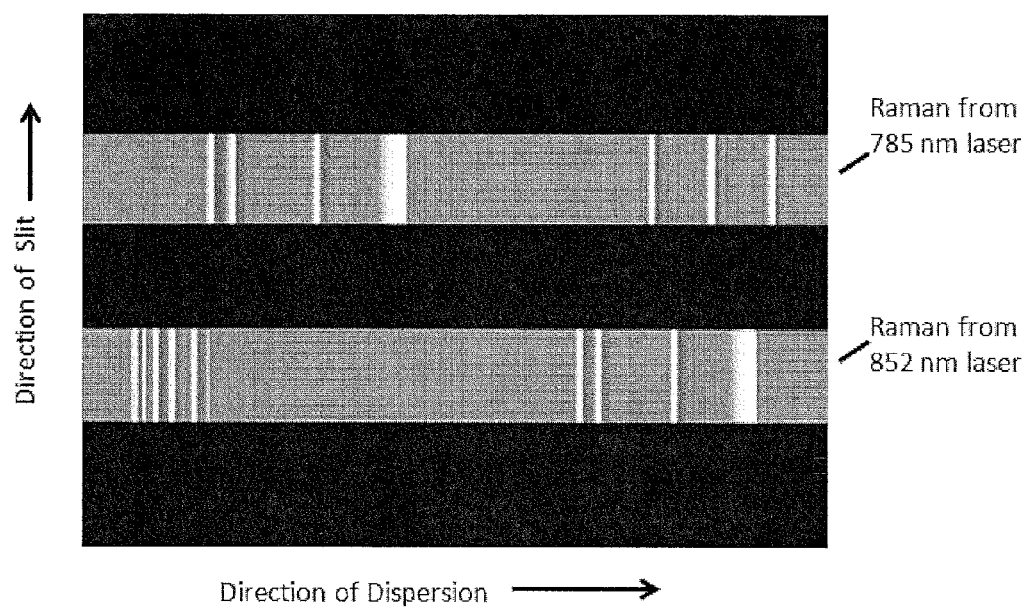
FIG. 14 is a Raman image after being dispersed by a spectrograph and projected onto a CCD.
Figure 15:
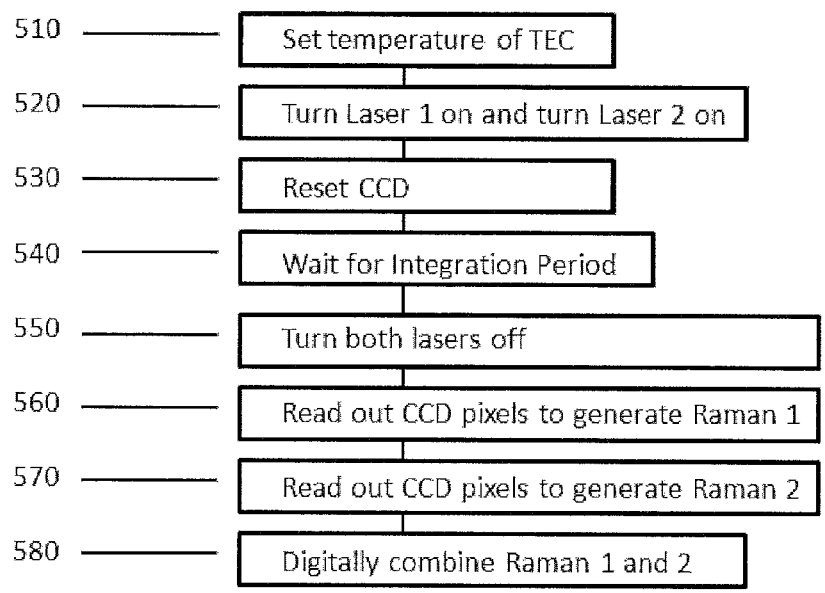
FIG. 15 is another flow diagram of a method for operating the spectrometer of FIGS. 1 and 2.

As described above, the Raman images projected onto the slit of the spectrograph 70 by the lasers 100 and 101 can be overlapped or separated to some degree. In the following example, the optics and laser spacing are such that the images are separated to some degree. An example of such an image after being dispersed by the spectrograph and then projected onto the CCD detector 80 is shown in FIG. 14. Since the CCD detector 80 is a two-dimensional array of detector elements (pixels), the CCD detector 80 is capable of detecting both the Raman spectrum generated from the first laser 100 and the Raman spectrum generated from the second laser 101 substantially simultaneously. The Raman spectrum is spatially separated along the axis of the CCD detector 80 which is aligned with the slit, and the spectra are dispersed along the remaining dimension. Dark region of the CCD detector 80 shown in FIG. 14 correspond to the absence of light, and white regions correspond to peaks in the corresponding spectrum. The beginning of the top spectrum (generated by the 785 nm wavelength laser 100) corresponds to the end of the bottom spectrum (generated by the 852 nm wavelength laser 101). Since the spectra do not overlap, both spectra are acquired simultaneously and the integrity of the two spectra are maintained by reading out the respective rows of pixels for each spectrum. Such a mode of operation is depicted in the flow diagram FIG. 15 and described below.

In step 510, the temperature of the thermoelectric cooler 205 is set to a predetermined value. In step 520, both lasers 100 and 101 are turned on. In step 530, the CCD detector 80 is reset to clear the detector of any accumulated charge. In step 540, a waiting period corresponding to a predetermined integration time is carried out. In the step 550, the lasers 100 and 101 are turned off. In step 560, the rows of pixels corresponding to the Raman generated by the DBR diode laser 100 are read out of the CCD detector 80 and a first Raman spectrum is generated. In the step 570, the rows of pixels corresponding to the Raman generated by the second laser 101 are read out of the CCD detector 80 and a second Raman spectrum is generated. The two Raman spectra are then digitally combined in step 580.

When the lasers 100 and 101 are excited simultaneously, the laser beams may be spatially discrete from one another (e.g., follow different paths) and/or illuminate different portions (e.g., adjacent portions) of the sample. In contrast, when the lasers 100 and 101 are excited sequentially, the laser beams may or may not be spatially discrete and/or illuminate different portions of the sample. The spectrometer therefore may acquire information from the same portion of the sample when sequentially exciting the lasers 100 and 101.

Example 2

Figure 16:
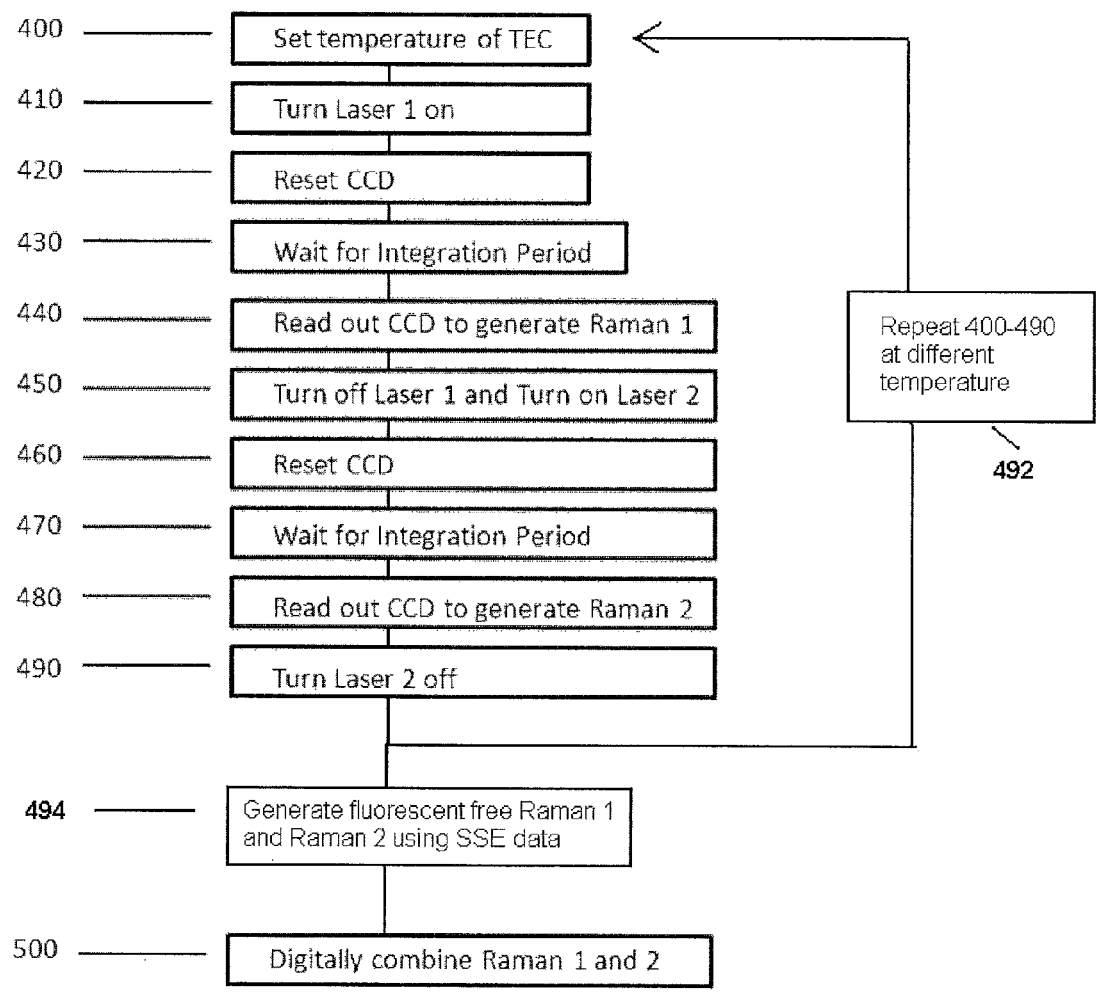
FIG. 16 is another flow diagram of a method for operating the spectrometer of FIGS. 1 and 2.

Removal of Fluorescence Background Using Sequentially Shifted Excitation Wavelengths As described above, both of the lasers 100 and 101 may be mounted onto the same thermoelectric cooler 205. In a previous patent, we described the advantages of a Sequentially Shifted Excitation (SSE) Raman instrument that allowed for the elimination of fluorescence backgrounds. In this SSE method, three or more Raman spectra are acquired for each laser while the laser is maintained at different temperatures for each of the three or more spectral acquisitions. In contrast, by having both of the lasers 100 and 101 mounted onto the same thermoelectric cooler, the SSE Raman data may be simply acquired as shown in the flow diagram of FIG. 16. In step 492, collection of the Raman 1 and Raman 2 are repeated after setting the thermoelectric cooler 205 to a different temperature. By carrying out the step 492 at least twice, there will be at least three SSE Raman 1 and three SSE Raman 2 spectra which may be processed as described above in the step 494 to yield fluorescence-free Raman 1 and Raman 2. This acquisition of SSE Raman data is also easily applied to additional spectral acquisition schemes such as that shown in FIG. 15.

Example 3

Synchronization of Events Using Microcontroller

A microcontroller may be used to control the collection of the Raman spectrum and to synchronize data collection, laser toggling, and temperature control. Although a variety of ways can be used to carry out the embodiments of the present invention, a significant advantage is realized when a single microcontroller is used to control the following events: turning the lasers on and off, setting the thermoelectric cooler set point, turning the thermoelectric cooler on and off, and controlling the CCD detector. By using a microcontroller to synchronize these events, the embodiments of the present invention can be carried out in a deterministic fashion and in a minimal amount of time, while still offering the user the flexibility to alter the sequence of events to gain additional advantages.

In some embodiments, the lasers 100 and 101 may be excited sequentially by turning one of the lasers 100, 101 on and off before turning the other laser 101, 100 on and off as described above. In other embodiments, the lasers 100 and 101 may be excited sequentially by turning one of the lasers 100, 101 on and then turning the other laser 101, 100 on. The first excited laser 100, 101 may subsequently be turned off before the second excited laser 101, 100 is turned off, or vice versa. In such embodiments, the laser beams of the lasers 100 and 101 may be spatially discrete and the spectra may be collected simultaneously, or sequentially. Alternatively, the laser beams of the lasers 100 and 101 may not be spatially discrete and the spectra may be collected sequentially.

The invention has been described with reference to various embodiments. It will be understood, however, that various aspects or details of the invention may be changed, or various aspects or details of different embodiments may be arbitrarily combined, if practicable, without departing from the scope of the invention. For example, one or more of the lasers 100 and 101 may be configured to produce laser beams with wavelengths other than those described above. The first laser 100 and the second laser 101, for example, may respectively produce laser beams with discrete (e.g., unique) wavelengths between about 200 nm and about 1100 nm. In addition, the laser filter 20 may pass a first wavelength band between about 200 nm and about 1100 nm, and a second wavelength band between about 200 nm and about 1100 nm that is different than the first wavelength band. In another example, one or more of the foregoing method steps may be re-ordered; e.g., the step 420 may be performed before the step 410, etc. In still another example, the excitation source 300 may include a multi-laser package configured with more than two lasers that divides the vibrational spectrum in more than two parts. In such an embodiment, the laser filter 20 may correspondingly pass more than two discrete wavelength bands. The foregoing description therefore is provided for the purpose of illustration only, and not for the purpose of limiting the invention which is defined solely by the appended claims.

Although the present invention has been illustrated and described with respect to several preferred embodiments thereof, various changes, omissions and additions to the form and detail thereof, may be made therein, without departing from the spirit and scope of the invention.

What is claimed is:

1. A spectrometer for acquiring a Raman spectrum from a sample, the spectrometer comprising:
a dual laser package including a first laser, a second laser and a mount located within an excitation source housing, wherein the first laser produces a first laser beam for generating a first Raman spectra from the sample, and the second laser produces a second laser beam for generating a second Raman spectra from the sample, wherein at least one of the first laser or the second laser each comprises a distributed Bragg reflector diode laser and the first laser is electrically coupled to a conductive first pad on the mount and the second laser is electrically coupled a conductive second pad on the mount, and the conductive first and second pads are electrically isolated from one another;
a detector adapted to collect the first Raman spectra and the second Raman spectra;
a processor that processes the collected first and second Raman spectra to provide the Raman spectrum,
the first laser beam has a first wavelength; and
the second laser beam has a second wavelength that is different than the first wavelength.

2. The spectrometer of claim 1, wherein the first laser and the second laser are configured to respectively produce the first laser beam and the second laser beam simultaneously.

3. The spectrometer of claim 1, wherein the first laser and the second laser are configured to respectively produce the first laser beam and the second laser beam sequentially.

4. The spectrometer of claim 1, wherein the first laser and the second laser are hermetically sealed within the excitation source housing.

5. The spectrometer of claim 1, wherein the excitation source housing includes a window through which the first laser beam and the second laser beam are directed out of the excitation source housing.

6. The spectrometer of claim 1, further comprising
a conductive third pad on the mount; and
a conductive fourth pad on the mount.

7. The spectrometer of claim 1, wherein the dual laser package further includes a thermistor that is electrically coupled to a conductive third pad on the mount and a conductive fourth pad on the mount.

8. The spectrometer of claim 1, wherein the dual laser package further includes a thermoelectric cooler to which the mount is attached.

9. The spectrometer of claim 1, wherein the detector comprises a charged couple device detector.

10. The spectrometer of claim 1, further comprising a laser filter through which the first laser beam and the second laser beam travel towards the sample, wherein the laser filter passes two discrete wavelength bands of light that correspond to wavelengths of the first and the second laser beams.

11. The spectrometer of claim 10, wherein the wavelength bands are between about 200 nm and about 1100 nm.

12. The spectrometer of claim 1, where the excitation source housing comprises a TOSA electronic package.

13. A spectrometer for acquiring a Raman spectrum from a sample, the spectrometer comprising:
a dual laser package including a first laser, a second laser and a mount located within an excitation source housing, wherein the first laser produces a first laser beam with a first wavelength for generating a first Raman spectra from the sample during a first mode of operation and the second laser produces a second laser beam with second wavelength for generating a second Raman spectra from the sample during a second mode of operation, wherein the first wavelength is different than the second wavelength, and where the first laser is electrically coupled to a conductive first pad on the mount and the second laser is electrically coupled a conductive second pad on the mount and the conductive first pad is electrically isolated from the conductive second pad;
a detector adapted to collect the Raman spectra;

a processor that combines the Raman spectra collected during the first and the second modes of operation to provide the Raman spectrum, the first laser beam has a first wavelength; and the second laser beam has a second wavelength that is different than the first wavelength.

14. A spectrometer for acquiring a Raman spectrum from a sample, the spectrometer comprising:

a distributed Bragg reflector diode first laser that produces a first laser beam for generating first Raman spectra from the sample, where the distributed Bragg reflector diode first laser is electrically coupled to a conductive first pad on a mount;

a distributed Bragg reflector diode second laser that produces a second laser beam for generating second Raman spectra from the sample, where the distributed Bragg reflector diode second laser is electrically coupled to a conductive second pad on the mount, where the mount, the distributed Bragg reflector diode first laser and the distributed Bragg reflector diode second laser are located within an excitation source housing; and a detector adapted to collect the first Raman spectra and the second Raman spectra, the first laser beam has a first wavelength; and the second laser beam has a second wavelength that is different than the first wavelength.

15. The spectrometer of claim 14, further comprising a processor that processes the collected first and second Raman spectra to provide the Raman spectrum.

16. A spectrometer for acquiring a Raman spectrum from a sample, the spectrometer comprising:

a dual laser package including a first laser, a second laser and a mount located within an excitation source housing, wherein the first laser produces a first laser beam for generating a first Raman spectra from the sample, and the second laser produces a second laser beam for generating a second Raman spectra from the sample, wherein at least one of the first laser or the second laser each comprises a distributed Bragg reflector diode laser and the first laser is electrically coupled to a conductive first pad on the mount and the second laser is electrically coupled a conductive second pad on the mount, where the conductive first and second pads are electrically isolated from one another;

a laser filter that received the first laser beam and the second laser beam, and provides two discrete wavelength bands of laser beam light;

a detector that collects the Raman spectra, the first laser beam has a first wavelength; and the second laser beam has a second wavelength that is different than the first wavelength.

17. A method for acquiring a Raman spectrum from a sample, the method comprising:

directing a first laser beam from a Bragg reflector diode first laser onto the sample to generate a first Raman spectra from the sample, where the distributed Bragg reflector diode first laser is electrically coupled to a conductive first pad on a mount, wherein the first laser beam has a first wavelength;

directing a second laser beam from a Bragg reflector diode second laser onto the sample to generate a second Raman spectra from the sample, where the distributed Bragg reflector diode second laser is electrically coupled to a conductive second pad on a mount that is electrically isolated from the conductive first pad, wherein the second laser beam has a second wavelength that is different than the first wavelength, where the mount, the distributed Bragg reflector diode first laser and the distributed Bragg reflector diode second laser are located within an excitation source housing;

collecting the first Raman spectra and the second Raman spectra with a detector;

combining the collected first Raman spectra with the collected second Raman spectra to provide the Raman spectrum, the first laser beam has a first wavelength; and the second laser beam has a second wavelength that is different than the first wavelength.

18. The method of claim 17, wherein the first wavelength is between about 200 nm and about 1100 nm; and the second wavelength is between about 200 nm and about 1100 nm.

19. The method of claim 17, wherein the first laser beam and the second laser beam are sequentially directed onto the sample.

20. The method of claim 17, further comprising:

directing the first laser beam through a laser filter; and directing the second laser beam through the laser filter;

wherein the laser filter is adapted to pass two discrete wavelength bands of light.

21. The spectrometer of claim 20, wherein the wavelength bands are between about 200 nm and about 1100 nm.

22. The method of claim 17, further comprising:

initializing the detector at a first point in time; and collecting the first Raman spectra with the detector for a first period of time that begins at the first point in time.

23. The method of claim 22, further comprising:

initializing the detector at a second point in time; and collecting the second Raman spectra with the detector for a second period of time that begins at the second point in time.

24. The method of claim 17, wherein the first laser beam and the second laser beam are directed onto the sample simultaneously.

* * * * *